US00PP16483P3

(12) United States Plant Patent
Benardella

(10) Patent No.: US PP16,483 P3
(45) Date of Patent: Apr. 25, 2006

(54) MINIATURE ROSE PLANT NAMED 'BENFEBU'

(50) Latin Name: *Rosa hybrida*
Varietal Denomination: BENfebu

(75) Inventor: Frank Benardella, Englishtown, NJ (US)

(73) Assignee: Nor'East Miniature Rose, Arroyo Grande, CA (US)

( * ) Notice: Subject to any disclaimer, the term of this patent is extended or adjusted under 35 U.S.C. 154(b) by 0 days.

(21) Appl. No.: 10/318,843

(22) Filed: Dec. 13, 2002

(65) Prior Publication Data

US 2004/0117879 P1 Jun. 17, 2004

(51) Int. Cl.
*A01H 5/00* (2006.01)

(52) U.S. Cl. ..... Plt./122
(58) Field of Classification Search ..... Plt./122
See application file for complete search history.

(56) References Cited

U.S. PATENT DOCUMENTS

PP4,231 P * 3/1978 Moore ..... Plt./118
PP4,598 P * 9/1980 Saville ..... Plt./116
PP5,857 P * 1/1987 Benardella ..... Plt./116
PP5,925 P * 4/1987 Benardella ..... Plt./122
PP8,020 P * 11/1992 Benardella ..... Plt./123

OTHER PUBLICATIONS http://www.stsrv.com/irar/newregis.asp Recent registrations from the IRAR, pp. 1 and 2.*
http://www.helpmefind.com/rose/pl.php?n=39693 'Merlot'.*

* cited by examiner

*Primary Examiner*—Kent Bell
*Assistant Examiner*—W. C. Haas

(57) ABSTRACT

'BENfebu' is a new and distinct variety of miniature rose plant primarily identified by its dark red flowers and petals of flushed white reverse, of hybrid tea form. There is little fade to the color of the flowers. Borne mostly in small clusters of 3 to 4, there are enough borne singly to use for exhibition cut flowers. The plant is upright, well branched and vigorous, clothed in dark green semi-glossy foliage.

1 Drawing Sheet

CROSS REFERENCE

The present invention bares some resemblance to 'BENmjul' (U.S. Plant patent application Ser. No. 10/035,940 filed Dec. 21, 2001, abandoned) from the same breeding program with which it shares some of the same parentage. More specifically, the seed parent of this new invention is 'BENfig' (U.S. Plant Pat. No. 8,020) which is a cross of 'Rise 'n' Shine' (U.S. Plant Pat. No. 4,231) by 'Laguna' (not under patent protection) and the seed parent of 'BENmjul' is 'BENjen' (U.S. Plant Pat. No. 5,857) which is a cross of 'Party Girl' (U.S. Plant Pat No. 4,598) by 'Laguna' and further that the seed parent of 'Party Girl' is 'Rise 'n' Shine'. Both cultivars have dark red buds and flowers of similar size and petal count on upright, well-branched plants. There are 2 primary differences between BENmjul and the new cultivar. The new cultivar has more of its dark red flowers borne in clusters and that the reverse of these petals is flushed with white while on 'BENmjul' the dark red flowers are borne mostly singly on longer stems and the reverse of its petals is only a slightly lighter shade of red. Additionally, the anthocyanin coloration of the stems and foliage is mostly absent on this new invention while it is strong on BENmjul.

Genus and species: *Rosa hybrida.*

Varietal denomination: 'BENfebu'.

BACKGROUND OF THE INVENTION

This present invention relates to a new and distinct variety of hardy, bush type plant of the miniature rose class and with exhibition form, the primary objective of this breeding program. This new variety is from a single seedling created in a greenhouse in Englishtown, N.J. by crossing the following two rose plants:

The seed parent is 'BENfig' (U.S. Plant Pat. No. 8,020).

The pollen parent is an unnamed, unintroduced miniature rose (not patented) which was a cross of 'KINfancy' (not patented) by 'BENblack' (U.S. Plant Pat. No. 5,925).

This present invention bares resemblance to its seed parent, BENfig (U.S. Plant Pat. No. 8,020), with a similar bud shape and petal count and size. The differences between those two plants are that the flowers of this new invention are a dark red with a lighter reverse as compared to light pink flowers with a lighter reverse on the seed parent and this new invention has a more compact plant habit. The primary trait from its pollen parent is its red coloring.

Asexual reproduction by cuttings of this new variety in Englishtown, N.J. and Rowley, Mass. shows that all distinguishing characteristics of this rose continually come true to form.

SUMMARY OF THE INVENTION

The present invention relates to a new and distinct variety of hardy dwarf bush type rose plant of the miniature class; the variety being primarily characteristized—as to novelty—by it's small, hybrid tea form, dark red blooms flushed white on the reverse.

The variety is further characterized by:

An abundance of these flowers borne mostly in small clusters of 3 or 4 but also singly Semi-glossy foliage A slight rose fragrance A plant which has good vigor, is upright and well branched.

A plant which grows and blooms satisfactorily both in the greenhouse and outdoors; provides decoration as a garden perennial, specimen plant or in large containers and is good for cut flowers and exhibition.

BRIEF DESCRIPTION OF THE DRAWING

The accompanying drawing is two color photographs of buds, flowers and foliage of this new variety in different stages of development.

The larger photograph was taken in February in San Luis Obispo County in California from specimens grown in an open-roof greenhouse (no covering by day).

The inset photograph, showing a typical hip, was taken in October in Essex County, Mass. from plants grown under plastic.

BOTANICAL DESCRIPTION OF THE PLANT

Following is a detailed description in outline form pertaining specifically to this new and distinct variety of miniature rose plant as observed during the summer months at between 4 and 5 years of age grown in Essex County, Mass. in an 8 inch standard nursery container in a peat moss and perlite based soilless mixture with a constant liquid feed program at an unknown amount below optimum levels; in a plastic covered greenhouse with climatic controls limited to a hot air furnace and only fan and vent cooling, allowing for great fluctuations in temperature, seasonally, as is typical under such conditions in New England. All major color plate identifications made are referring to The Royal Horticultural Society Colour Chart except where common terms of color definition are employed.

Genus/species: *Rosa hybrida* 'minima'.
Varietal denomination: 'BENfebu'.
Commercial class: Miniature Rose.
Seed parent: 'BENfig' (U.S. Plant Pat. No. 8,020).
Pollen parent: A seedling which was a cross of 'KINfancy' (not patented) by 'BENblack' (U.S. Plant Pat. No. 5,925).

FLOWERS

Blooming habit: Recurrent.

Borne: Mostly in small clusters of 3 or 4 flowers, but also singly.

Bud:

*Size.*—11/16 to 15/16 of an inch in length and ½ in diameter at the widest point just before the sepals divide.

*Form.*—Narrow ovate.

*Sepals.*—Color — an olive green, near 146B and inside surface lighter, near 147C and with 147B along the margins of the interior. Size — 1 to 1 1/16 inch long and 5/16 inch wide excluding any foliation; extending ½ to ¾ inch beyond the tip of the bud just before they start to divide. Characteristics — lanceolate; 2 innermost sepals with smooth edges and the 3 outermost sepals are very finely beaded with 1 to 3 narrow, foliar appendages on one or both edges; rolling back first to a 90 degree angle with the receptacle; as the petals start to unfurl, rolling back almost to the stem and as the hip forms and matures returning to and remaining at a 90 degree angle with the receptacle. Surface texture — inside surface pubescence; the outer surface is glabrous.

*Peduncle.*—Length — averaging ⅞ inch. Diameter — most often 7/64 inch, occasionally only 6/64 inch. Aspect — straight. Strength — strong, erect. Color — yellow green, near 144B, anthocyanin coloration absent. Texture — usually with a medium amount of stiff hairs.

*Receptacle.*—Diameter — about 5/16 inch. Color — near 144A. Texture — glabrous.

*Color.*—When sepals first divide — a medium red, near 57B.

Bloom:

*Size.*—When fully expanded — most often 2 inches across and ⅞ inch deep measured from the top of the receptacle; diameter and depth vary in respect to bud length with the flower depth equal to the bud length and the flower diameter being slightly greater than twice the bud length, by about ⅛ inch.

*Form.*—High centered at first with petals reflexing slightly as they start to unfurl and when full open having a flattened convex upper profile and a flat lower profile with petals remaining only slightly reflexed.

*Petalage.*—23 to 28.

*Petaloids.*—1 or up to 7.

*Fragrance.*—Slight.

*Persistence.*—Usually drops off cleanly in 6 to 10 days.

*Lasting quality as cut flower.*—4 to 8 days.

Petals:

*Texture.*—Glabrous.

*Appearance.*—Inside — velvety, outside — satiny.

*Form.*—Broad fan shaped, rounded base; margins with a very slight undulation and usually without a definitive apex on the outer petals and sometimes a very minute serration near the center of the outer margin on some of the inner petals; reflexing of margins is slight.

*Length and width in inches.*—As wide as they are long — 1 inch by 1 inch to 1⅛ inches by 1⅛ inches.

*Arrangement.*—Arranged shingle-like.

*Color.*—During the first few days — inner and outer petals are a dark cardinal red, with inner petals being between 53A and 46A and outer petals being between 53B and 46B; the reverse is flushed with white giving the appearance of being near 66C as in the smaller inset image in the accompanying drawing and occasionally with one or two of the petals having a streak up through their center, which is a very pale yellow, near 4D. When half blown — both inner and outer petals are between 53B and 46B and the reverse remaining near 66C. Seasonal differences — in October, the reverse of the petals is only lightly flushed and always being near 53C, as depicted in the larger of the accompanying images; the upper surface color is very near the same as in the summer with no visible difference. Variegations — although the upper surface of most of the petals is a solid cardinal red some of the inner petals may have a streak of very light yellow, near 4D, up through the center. When there are streaked petals within a flower, there is usually 3 or more but never more than 7 petals with the streak and they are not usually adjacent to one another. As previously noted, some of the outer petals may have the very light streak going up the middle of the reverse.

*Base of petals.*—Near 4D and going about 1/5 of the way up the petals.

*Petals at point of attachment.*—Near 6D. As the bloom ages there is little change in the color as it lightens only slightly, remaining near 53B.

*General tonality.*—Dark red.

Petaloids:

*Color.*—Same as that of the inner petals except there is apt to be more of the very light yellow, near 4D, streaking up from the base to the tip.

*Size.*—Width — 3/4 inch at the widest point. Length — quite variable from 1/4 inch to 7/16 inch.

REPRODUCTIVE ORGANS

Stamens, filaments and anthers:

*Arrangement.*—Regularly arranged around styles. Quantity: 120 to 130.

*Filaments.*—Length — varying 4/32 to 11/32 inch. General color — light yellow, near 8C.

*Anthers.*—Color — light yellow but slightly darker than the filaments, near 10C.

Pollen:

*Color.*—A medium orange yellow, near 21C.

*Quantity.*—Ample.

Pistils, styles and stigmas:

*Quantity.*—About half or a few less than half as many as stamens.

*Styles.*—Thin; uneven length between 1/8 and 2/8 inch. Color — translucent, light yellow green at their base, near 2D, and becoming just a light translucent, empire yellow, near 11D upward from the base.

*Stigmas.*—Color — a light mimosa yellow, just a shade darker than the upper portion of the styles, near 8D.

Hips:

*Shape.*—Pumpkin shaped, smooth surface; seeds are entirely enclosed within the hip.

*Size.*—Usually 11/16 inch in diameter.

*Quantity.*—20 or more hips per plant.

*Color.*—Becoming near 169B from the grayed-orange group.

*Seed.*—Color — a light "grayed" yellow, between 162C and 162D. Size — averaging 5/32 inch diameter, obovate shape and irregular sides.

PLANT

Habit: Upright and well branched.

Growth: Vigorous and uniformly branched, maturing at a height between 26 and 34 inches and a width of 30 to 36 inches.

Length and diameter of stems:

*Main stems.*—Potential length is unknown as the observed plants have been cut back numerous times; usually 9/32 inch diameter.

*Primary laterals.*—Usually 5½ inches long with a range of 4⅞ inches to 6 inches, and a diameter of 7/32 to 8/32 inch.

*Secondary laterals.*—Usually 2½ inches long and occasionally up to 3 inches long and a diameter of 5/32 to 6/32 inch.

*Candelabra stems* (*those stems which originate at or near the base of the plant and grow straight and quickly to a length equal to or greater than the crown of the plant and culminate with a cluster of flowers, usually during seasons when day and night temperatures fluctuate more than* 20 *degrees Fahrenheit*).—15/32 inch diameter at the base of a mature plant and tapering by 1/32 inch for approximately every 1¼ inches in stem length and may reach up to 32 inches before ending at a peduncle with a cluster of flowers. Primary laterals originating from a candelabra on a mature plant — a diameter of 11/32 inch near the point of attachment to the candelabra and tapering as does the candelabra; the length of the primary laterals from the candelabras is such as to bring them to the same length as the candelabra to which they are attached; therefore, primary laterals originating closer to the tip of the candelabra to which they are attached are shorter than those originating closer to the base. A candelabra may send out 2 or 3 laterals after the end of each bloom cycle and usually from random locations along the stem.

Length and diameter of flowering stem: Length averages 6 to 9 inches with any flowering stems originating from a candelabra being greater than 6½ inches and most often are 8½ to 10 inches long; diameter is usually 5/32 inch near the point of attachment and tapering quickly to and reaming at 4/32 inch to the peduncle.

Length of internodes: Spacing between nodes is erratic with the most frequently found lengths being 1⅛ inches and 1⅜ inches; the largest spacing is usually near the middle of the stem; the pair of nodes closest to the point of attachment of a stem is most often 1 3/16 inches and may occasionally be as short as ⅞ inch; the next node is always a greater distance away; the node following that is usually further still but not by uniform increases. The last node on the stem before a peduncle is always a bit closer. Internode measurements for five stems are shown here:

| | | | | |
|---|---|---|---|---|
| Stem #1: | ⅞" | 1½" | 2¼" | 1⅛" |
| Stem #2: | ⅞" | 1⅛" | 1⅜" | 1 3/16 |
| Stem #3: | 1 3/16" | 1 10/16" | 1 15/16" | 1 5/16" |
| Stem #4: | 1 3/16" | 2¼" | 1 7/16" | |
| Stem #5: | 1" | 1 7/16" | 1 15/16" | 1⅜ |

Internode length on candelabras is even more erratic, sometimes gradually decreasing in length proceeding all the way up the stem, but sometimes starting from the base and decreasing in length proceeding up the stem then increasing in length around the middle of the stem and then decreasing again towards the tip. Lengths of internodes on the candelabras may be any of those measurements as given for the internodes of the stems.

Foliage: Near pinnately compound (some leaflets, most often the basal ones, are not directly opposite by as much as 1/32 inch) with 5 leaflets, occasionally with 3 or 7.

*Size of mature leaf.*—3½ to 3¼ inches from plant stem to tip when measured along the rachis; mature terminal leaflet — 1¼ to 1⅞ inches from base to tip and 13/16 to 15/16 inch wide at its widest part.

*Quantity.*—Abundant, excluding candelabras, all stems usually have 5 leaves regardless of the length of the stem but occasionally some of the shorter stems having only 3 leaves.

*Leaflets.*—Shape — ovate, tapering towards both ends, to an acuminate apex and a narrow oval base. Color — new foliage, upper surface, 137A, under surface near 137B; older foliage — a very dark green, near 147A, on the upper surface and a medium green, near 147B, on the reverse; anthocyanin coloration is absent. Appearance — upper surface, semi-glossy; underside, matte with veins protruding slightly of a light olive green, near 144C, Texture — both surfaces are glabrous under surface — lightly textured from veins and leathery. Edge — fine, near even serration and with stipate glands unevenly spaced along the entire margin, often on the outer point of the serration.

*Petiole rachis.*—Infrequently having 1 to 3 undeveloped basal leaflets which sometimes appear as tiny leaflets and other times as very tiny appendages, not always evenly spaced or opposite. Color on old leaf — upper side is an dark olive green, between 147A and 146A, underside near 144A. Color on young leaf — upper side is a medium green, near 137C; the underside is near 144A. Texture — moderately smooth; upper side is shallowy grooved with some stipate glands on the edges of the grooves; the underside is very smooth with a few stipate glands and occasionally 1 to 3 prickles. Rachis — length varies from 2⅝ to 2⁵⁄₁₆ inch.

*Petiolules.*—Color — on old leaf, upper side is a lighter olive green than the rachis, near 147C, and the underside is also lighter, near 144C; on young leaf, the color is the same as that of the petiole/rachis on both surfaces. Size — usually 1/32 of an inch long but sometimes even shorter to the point of appearing non existent.

*Stipules.*—Very narrow, measuring ¹⁰⁄₁₆ to ¹¹⁄₁₆ inch in length; margin — fine and uneven serrulation and the very edge tightly reflexing on the mature leaf.

Resistance: Good resistance to downy and powdery mildews and insects; average resistance to blackspot; no rust observed.

Wood:

*New wood.*—Texture — smooth, glabrous; color — near 146A.

*Old wood.*—Color — between 147B and 146C and having areas of very slightly raised and corky-textured surface near 199B and, as the plant continues to age, the old wood becomes entirely covered with the slightly raised, corky-textured surface of near 199B.

Thorns:

*Quantity.*—On main stalks and laterals, few, one or less per inch of stem. On main stalks and laterals of candelabra growth, ordinary for a miniature rose, having 2 or 3 thorns per inch of stem.

*Form.*—An elliptical base tapering to a fine point, straight and angled slightly down, being ¼ to ³⁄₁₆ inch in length.

*Color when young.*—A medium shade of yellow green, near 151A.

*Color when old.*—Near 164B from the greyed-orange group.

*Prickles.*—1 to 3 occasionally found on underside of the rachis only color: near 19D, Egyptian buff yellow.

Winter hardiness: Tested hardy in zones 4 through 9 with ample winter protection recommended zones 6 and colder.

Miniature Rose Patents Using the Word "minima" in Their Botanical Names as Published on the United States Patent and Trademark Office Web Site

| | Patent Number | Title (Where found) |
|---|---|---|
| 1. | PP14,894 | Miniature rose plant named 'BENminn' (Genus/species: *Rosa hybrida 'minima'*) |
| 2. | PP14,533 | Miniature rose plant named 'Benhile' (Genus/species: *Rosa 'minima'*) |
| 3. | PP13,056 | Miniature rose plant named 'SAVaralph' (Genus/species: *Rosa chinensis 'minima'*) |
| 4. | PP13,055 | Miniature rose plant named 'SAVapple' (Genus/species: *Rosa chinensis 'minima'*) |
| 5. | PP12,652 | Miniature rose plant named 'SAVacon' (BOTANICAL DESCRIPTION OF THE PLANT: *Rosa chinensis 'minima'*) |
| 6. | PP11,810 | Miniature rose plant named 'Savanade' (BACKGROUND OF THE INVENTION: *Rosa chinensis 'minima'*) |
| 7. | PP11,132 | Miniature rose plant named 'SAValute' (BACKGROUND OF THE INVENTION: *Rosa chinensis 'minima'*) |
| 8. | PP10,980 | Miniature rose plant named 'SAVabino' (BACKGROUND OF THE INVENTION: *Rosa chinensis 'minima'*) |
| 9. | PP9,798 | Miniature rose plant named 'Savamor' (BOTANICAL DESCRIPTION OF THE PLANT: Type: *Rosa chinensis 'minima'*) |
| 10. | PP9,790 | Miniature rose plant named 'WELangel' (BACKGROUND OF THE INVENTION: *Rosa chinensis 'minima'*) |
| 11. | PP9,785 | Miniature rose plant named 'SAVacook' (BACKGROUND OF THE INVENTION: *Rosa chinensis 'minima'*) |

What is claimed:

1. A new and distinct variety of hardy miniature rose plant is claimed, substantially as illustrated and described, characterized by dark red, non-fading blooms of hybrid tea form, showing a lighter reverse before it is full open on an upright, vigorous plant.

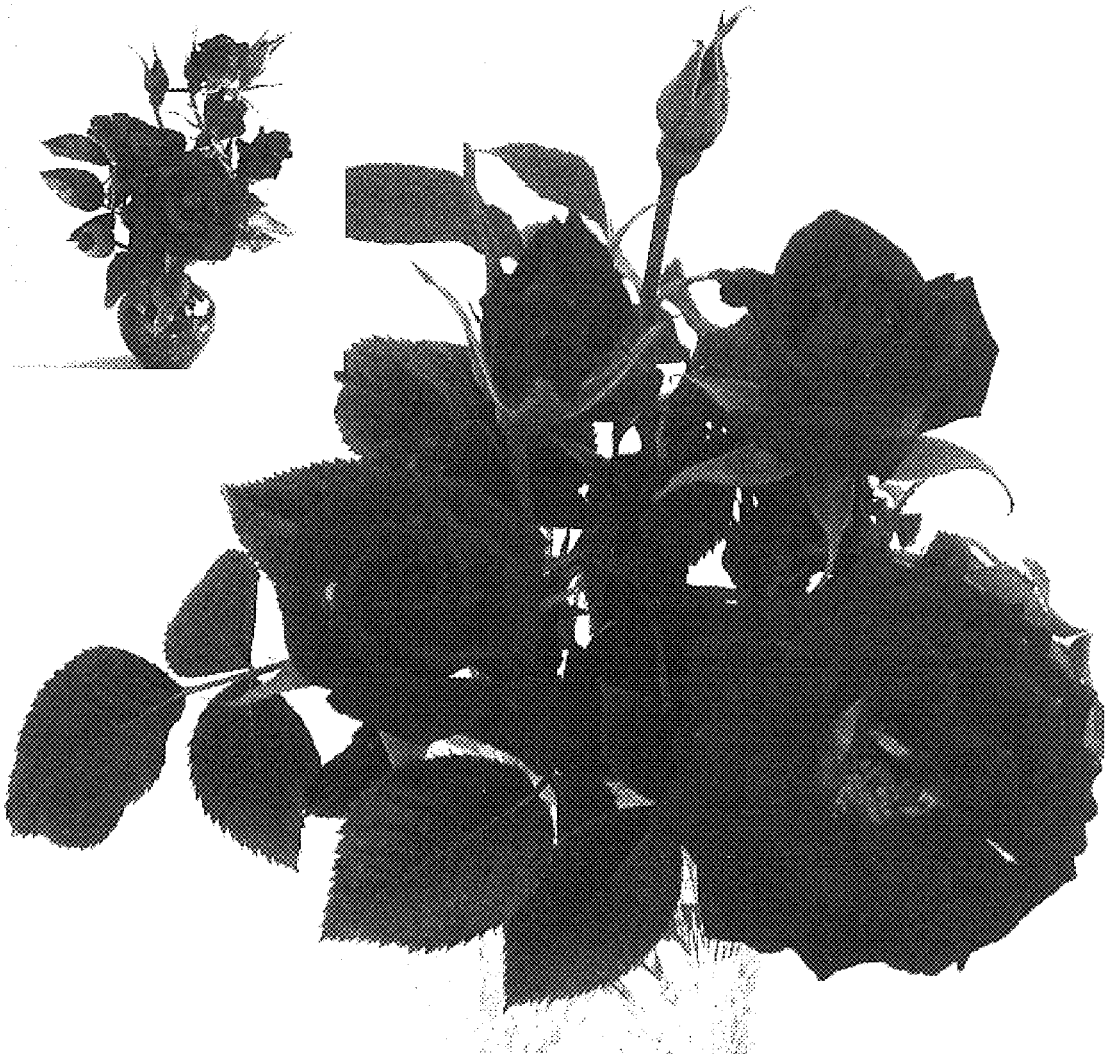

* * * * *